(12) United States Patent
Carlson et al.

(10) Patent No.: US 9,047,256 B2
(45) Date of Patent: Jun. 2, 2015

(54) SYSTEM AND METHOD FOR MONITORING AUDIENCE IN RESPONSE TO SIGNAGE

(75) Inventors: Alan Carlson, San Antonio, TX (US); Richard D. Wooden, Ogallala, NE (US)

(73) Assignee: iHeartMedia Management Services, Inc., San Antonio, TX (US)

( * ) Notice: Subject to any disclaimer, the term of this patent is extended or adjusted under 35 U.S.C. 154(b) by 597 days.

(21) Appl. No.: 12/649,583

(22) Filed: Dec. 30, 2009

(65) Prior Publication Data

US 2011/0161160 A1 Jun. 30, 2011

(51) Int. Cl.
- G06F 19/22 (2011.01)
- G06F 3/01 (2006.01)
- G06Q 30/02 (2012.01)
- G09F 27/00 (2006.01)
- G02B 27/00 (2006.01)

(52) U.S. Cl.
CPC ............ *G06F 19/22* (2013.01); *G02B 27/0093* (2013.01); *G06F 3/013* (2013.01); *G06Q 30/02* (2013.01); *G06Q 30/0242* (2013.01); *G09F 27/00* (2013.01)

(58) Field of Classification Search
CPC ... G06F 3/0219; G06Q 30/02; G06Q 30/0242
USPC .......................................... 705/14.41, 14.45
See application file for complete search history.

(56) References Cited

U.S. PATENT DOCUMENTS

| | | | |
|---|---|---|---|
| 5,231,674 A | 7/1993 | Cleveland et al. | |
| 5,861,940 A | 1/1999 | Robinson et al. | |
| 6,252,522 B1 | 6/2001 | Hampton et al. | |
| 6,459,446 B1 | 10/2002 | Harman | |
| 6,577,329 B1 | 6/2003 | Flickner et al. | |
| 6,601,021 B2 | 7/2003 | Card et al. | |
| 6,842,670 B2 | 1/2005 | Lin et al. | |
| 6,904,408 B1 | 6/2005 | McCarthy et al. | |

(Continued)

FOREIGN PATENT DOCUMENTS

| CA | 2 457 090 A1 | 2/2003 |
|---|---|---|
| CA | 2 545 202 A1 | 5/2005 |

(Continued)

OTHER PUBLICATIONS

"Eye tracking", *Wikipedia, the free encyclopedia* http://en.wikipedia.org/wiki/Eye_tracking (2009) Oct. 22.

*Primary Examiner* — Eric Netzloff
(74) *Attorney, Agent, or Firm* — Garlick & Markison; Edward J. Marshall (57) ABSTRACT

A system and method for monitoring media viewing activity by one or more individuals is disclosed. In general, the location of a sign can be identified, a human eye can be located and tracked and vectoring module and a projection module can determine if the individual's eyes are directed towards the sign. The content of the signage can be coordinated with the direction of the eye in real time to determine what content the individual viewed. An audience reaction module can acquire audience reaction data such as how long eyes are engaged on the sign and can determine other reactions such as a smile a frown or a gesture of interest or disinterest based on the change of content on the signage. The system allows for an advertiser to acquire and evaluate audience feedback related to presentation and content displayed on media (e.g., billboards, digital signage, window displays, etc.).

37 Claims, 6 Drawing Sheets

(56) References Cited

U.S. PATENT DOCUMENTS

| | | |
|---|---|---|
| 6,926,429 B2 | 8/2005 | Barlow et al. |
| 6,962,240 B2 | 11/2005 | DiFranza et al. |
| 6,972,733 B2 | 12/2005 | Maguire, Jr. |
| 7,044,602 B2 | 5/2006 | Chernyak |
| 7,120,880 B1 | 10/2006 | Dryer et al. |
| 7,261,415 B2 | 8/2007 | Chernyak |
| 7,331,671 B2 | 2/2008 | Hammoud |
| 7,344,251 B2 | 3/2008 | Marshall |
| 7,365,738 B2 | 4/2008 | Molander et al. |
| 7,391,887 B2 | 6/2008 | Durnell |
| 7,431,457 B2 | 10/2008 | Chernyak |
| 7,438,418 B2 | 10/2008 | Marshall |
| 7,495,631 B2 | 2/2009 | Bhakta et al. |
| 7,501,995 B2 | 3/2009 | Morita et al. |
| 7,529,772 B2 | 5/2009 | Singh |
| 7,561,143 B1 | 7/2009 | Milekic |
| 8,520,070 B1* | 8/2013 | Englander et al. ............ 348/148 |
| 2002/0075384 A1 | 6/2002 | Harman |
| 2003/0142041 A1 | 7/2003 | Barlow et al. |
| 2004/0117378 A1 | 6/2004 | Manandhar |
| 2004/0196214 A1 | 10/2004 | Maguire, Jr. |
| 2004/0196433 A1* | 10/2004 | Durnell ........................ 351/209 |
| 2004/0220704 A1 | 11/2004 | Lin et al. |
| 2004/0247183 A1 | 12/2004 | Molander |
| 2005/0116929 A1 | 6/2005 | Molander et al. |
| 2005/0175218 A1 | 8/2005 | Vertegaal et al. |
| 2005/0213792 A1 | 9/2005 | Hammoud |
| 2005/0264890 A1 | 12/2005 | Morrone et al. |
| 2005/0280603 A1 | 12/2005 | Aughey et al. |
| 2006/0109237 A1 | 5/2006 | Morita et al. |
| 2006/0110008 A1* | 5/2006 | Vertegaal et al. ............ 382/103 |
| 2006/0146046 A1 | 7/2006 | Longhurst et al. |
| 2006/0229939 A1 | 10/2006 | Bhakta et al. |
| 2006/0287913 A1 | 12/2006 | Baluja |
| 2007/0038516 A1 | 2/2007 | Apple et al. |
| 2007/0073585 A1 | 3/2007 | Apple et al. |
| 2007/0081090 A1 | 4/2007 | Singh |
| 2007/0105071 A1 | 5/2007 | Weatherhead |
| 2007/0205963 A1 | 9/2007 | Piccionelli et al. |
| 2007/0247422 A1 | 10/2007 | Vertegaal et al. |
| 2008/0143674 A1 | 6/2008 | Molander et al. |
| 2008/0259096 A1 | 10/2008 | Huston |
| 2009/0025023 A1 | 1/2009 | Pradeep et al. |
| 2009/0036755 A1 | 2/2009 | Pradeep et al. |
| 2009/0051561 A1* | 2/2009 | Cadavid .................... 340/691.6 |
| 2009/0062629 A1 | 3/2009 | Pradeep et al. |
| 2009/0062681 A1 | 3/2009 | Pradeep et al. |
| 2009/0097705 A1* | 4/2009 | Thorn ......................... 382/103 |
| 2009/0146775 A1 | 6/2009 | Bonnaud et al. |
| 2009/0177528 A1* | 7/2009 | Wu et al. ........................ 705/10 |
| 2009/0197616 A1 | 8/2009 | Lewis et al. |
| 2010/0253494 A1* | 10/2010 | Inoue ........................... 340/436 |
| 2010/0273139 A1* | 10/2010 | Doppelt et al. ............... 434/327 |
| 2011/0103595 A1* | 5/2011 | Ramaswamy et al. ......... 381/56 |

FOREIGN PATENT DOCUMENTS

| | | |
|---|---|---|
| CA | 2 435 873 C | 10/2008 |
| CN | 200962301 Y | 10/2007 |
| CN | 201035360 Y | 3/2008 |
| EP | 1 032 862 A1 | 9/2000 |
| EP | 1 333 410 A2 | 8/2003 |
| EP | 1 333 410 A3 | 8/2003 |
| EP | 1 583 035 A2 | 10/2005 |
| EP | 1 562 102 B1 | 3/2008 |
| GB | 2 408 164 A | 5/2005 |
| GB | 2 437 575 A | 10/2007 |
| JP | 2006-163900 A | 6/2006 |
| TW | 531402 | 5/2003 |
| WO | WO 99/27412 A1 | 6/1999 |
| WO | WO 00/72289 A1 | 11/2000 |
| WO | WO 03/017203 A1 | 2/2003 |
| WO | WO 2005/046465 A1 | 5/2005 |
| WO | WO 2006/100645 A2 | 9/2006 |
| WO | WO 2007/011092 A1 | 1/2007 |
| WO | WO 2007/022104 A2 | 2/2007 |
| WO | WO 2007/056287 A2 | 5/2007 |
| WO | WO 2006/100645 A3 | 7/2007 |
| WO | WO 2007/022104 A3 | 10/2007 |
| WO | WO 2007/056287 A3 | 12/2007 |
| WO | WO 2008/066460 A1 | 6/2008 |
| WO | WO 2008/141340 A1 | 11/2008 |
| WO | WO 2008/154410 A1 | 12/2008 |
| WO | WO 2009/099875 A2 | 8/2009 |

* cited by examiner

SYSTEM AND METHOD FOR MONITORING AUDIENCE IN RESPONSE TO SIGNAGE

TECHNICAL FIELD

Embodiments are generally related to the collection of audience response data for the generation and calculation of advertising metrics. Embodiments are additionally related to eye tracking devices

BACKGROUND OF THE INVENTION

Billboards are utilized to impart advertising information to passengers, drivers and pedestrians within view of the billboard. A typical billboard is a large outdoor advertising structure usually found in high traffic areas such as alongside busy roads. Billboards present large advertisements to passing pedestrians and drivers. Typically showing large, ostensibly witty slogans, and distinctive visuals, billboards are highly visible in the top designated market areas. Bulletins are the largest, most impactful standard-size billboards. Located primarily on major highways, expressways or principal arterials, they command high-density consumer exposure (mostly to vehicular traffic). Bulletins afford greatest visibility due not only to their size, but because they allow creative "customizing" through extensions and embellishments. Billboards are an ideal place to advertise business because rather than you having to find your customers, your customers will find your advertising Posters represent another common form of billboard advertising, located chiefly in commercial and industrial areas on primary and secondary arterial roads. Posters are a smaller format than bulletins and are viewed principally by residents and commuter traffic, with some pedestrian exposure. Yet smaller outdoor advertising displays are Kiosks, prevalent at buss stops, train stations, on and in busses, in subways, along busy walkways etc.

Most billboards and similar advertising media are static. Recently, however, the advertising industry has moved toward electronic billboards and similar digital displays, which are capable of imparting a wide variety of different types of advertisements in a single digital display over a shorter period of time.

Electronic billboards and electronic signs are most common in major cities such as Las Vegas, New York and Tokyo, where large-format electronic signs deliver advertising via static, periodic posting and dynamic video content to passersby. Although the display technologies may vary widely, electronic signs and billboards all require some type of content source to generate the images on the display. Depending on regulatory and technical considerations, this content can be a series of static slides (periodic postings), or a sequence of broadcast-quality video and animation.

One of the problems with such advertising media is the poor ability to track how often the advertisements actually reach an intended target or make an "impression" on passing drivers, pedestrians, passengers, and so forth. Current approaches to this problem do not readily enable tracking mobile viewers of billboard advertising, especially those in a vehicle (e.g., automobile, trucks, trains, etc).

BRIEF SUMMARY

The following summary is provided to facilitate an understanding of some of the innovative features unique to the disclosed embodiments and is not intended to be a full description. A full appreciation of the various aspects of the embodiments disclosed herein can be gained by taking the entire specification, claims, drawings, and abstract as a whole.

It is, therefore, one aspect of the disclosed embodiments to provide for an improved system and method for monitoring audience response to advertising activity.

It is another aspect of the disclosed embodiments to provide for a system and method for tracking responses of mobile viewers to different forms of advertising.

It is an additional aspect of the disclosed embodiments to provide a system and method for tracking the number of mobile viewers of billboard advertising, especially those traveling in a vehicle (e.g., automobile, trucks, trains, etc).

The aforementioned aspects and other objectives and advantages can now be achieved as described herein.

In accordance with one aspect of the disclosed embodiments, a system and method for monitoring media viewing activity is disclosed. In general, an eye tracking device is employed for monitoring the eyes of one or more individuals in a vehicle with respect to information displayed on media external to the vehicle and in view of the monitored individual. A surveillance device generates a view of the information displayed on media external to the vehicle. The surveillance device communicates with the eye tracking device in order to correlate data collected from the surveillance device and the eye tracking device, the data indicative of a positive posting of the information to thereby enable a valuation of the information displayed on the media (e.g., billboards, digital signage, window displays, etc.). Such a system and/or method thus enable eye tracking of mobile viewers in vehicles (automobiles or similar), including correlation of the eye movement and outdoor view to the actual surrounding billboard display devices.

In accordance with another aspect of the disclosed embodiments, a system for monitoring media viewing activity is disclosed. Such a system generally includes an eye tracking device for monitoring an eye of an individual (e.g., a driver or a passenger) in a vehicle with respect to information displayed on media external to the vehicle and in view of an individual in the vehicle. A surveillance device can be employed for generating a view of the information displayed on media external to the vehicle, the surveillance device in communication with the eye tracking device in order to correlate data collected from the surveillance device and the eye tracking device, the data indicative of a positive posting of the information to thereby enable a valuation of the information displayed on the media.

In such a system, the eye tracking device and the surveillance device are preferably attached to the vehicle. Additionally, a data-processing apparatus such as, for example, a processor can be provided for processing and correlating the data collected from the surveillance device and the eye tracking device. The processor is capable of communicating electronically with the eye tracking device and the surveillance device. Additionally, a solar powered device can be employed for providing electrical energy to the eye tracking device, the surveillance device, and/or the processor and associated components. A memory can also be utilized for storing information output by the eye tracking device and the surveillance device.

In accordance with another aspect of the disclosed embodiments, a method for monitoring media viewing activity is disclosed. In such an embodiment, a logical operational step can be implemented for monitoring utilizing an eye tracking device, at least one eye of at least one individual in a vehicle with respect to information displayed on media external to the vehicle and in view of the monitored individual. A logical operational step can be then implemented for generating a view of the information displayed on media external to the vehicle utilizing a surveillance device that communicates with the eye tracking device in order to thereafter correlate data collected from the surveillance device and the eye tracking device, so that the data is indicative of a positive posting of the information and thereby enables a valuation of the information displayed on the media. An additional logical operational step can include processing and correlating the data collected from the surveillance device and the eye tracking device utilizing a processor. Such a method can further include the step of storing in a memory information output by the eye tracking device and the surveillance device. Such a method can also include a step of providing electrical energy to the eye tracking device and the surveillance device utilizing a solar powered device.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

The particular values and configurations discussed in these non-limiting examples can be varied and are cited merely to illustrate at least one embodiment and are not intended to limit the scope thereof.

Figure 1:
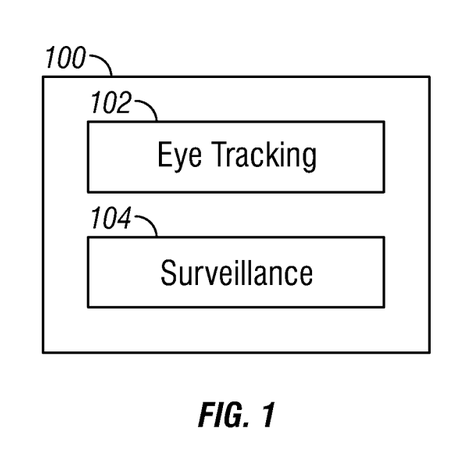
FIG. 1 illustrates a block diagram of a system for monitoring media viewing activity, in accordance with the disclosed embodiments.

FIG. 1 illustrates a block diagram of a system 100 for monitoring media viewing activity, in accordance with the disclosed embodiments. Note that in FIGS. 1-7, identical or similar parts or elements are indicated by identical reference numerals. System 100 depicted in FIG. 1 includes an eye tracking device 102 that monitors an eye of an individual in a vehicle, such as vehicle 304 of FIG. 3 with respect to information displayed on media external to the vehicle 304 and in view of the individual. System 100 also includes a surveillance device 104 for generating a view of the information displayed on media external to the vehicle 304. The surveillance device 104 communicates with the eye tracking device 102 in order to correlate data collected from the surveillance device 104 and the eye tracking device 102, the data indicative of a positive posting of the information to thereby enable a valuation of the information displayed on the media, such as, for example, billboard 302 depicted in FIG. 3.

Figure 2:
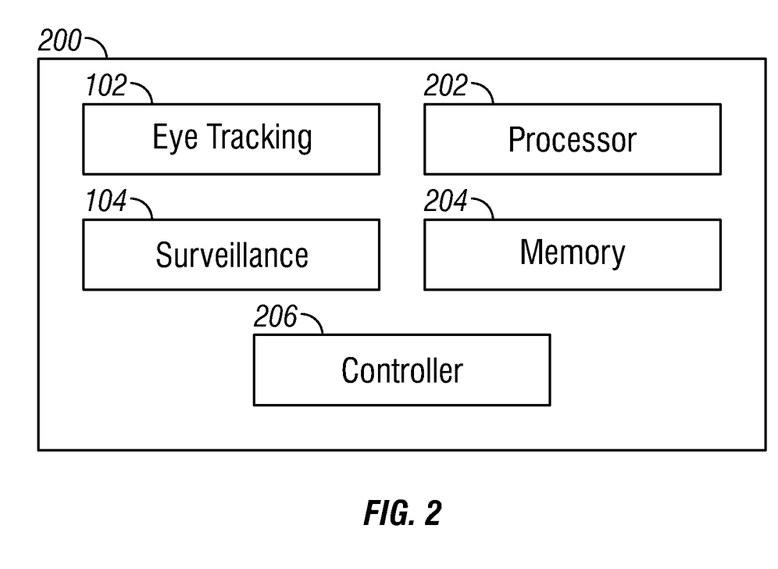
FIG. 2 illustrates a block diagram of a system for monitoring media viewing activity, in accordance with the disclosed embodiments.

FIG. 2 illustrates a block diagram of a system 200 for monitoring media viewing activity, in accordance with the disclosed embodiments. The configuration depicted in FIG. 2 is a variation to the system 100 illustrated in FIG. 1. System 200 includes the eye tracking device 102 for monitoring the eye(s) of an individual in the vehicle 304 with respect to information displayed on media (e.g., billboard 302) external to the vehicle and in view of the individual. System 200 also includes the surveillance device 104 for generating a view of the information displayed on media external to the vehicle 304. System 200 additionally includes a processor 202 for processing and correlating the data collected from the surveillance device 104 and the eye tracking device 102.

A memory 204 can also be included as a part of system 200 for storing information output by the eye tracking device 102 and the surveillance device 104. Note that the processor 202 can be implemented as, for example, a CPU (Central Processing Unit) or the portion of a data-processing system/apparatus (e.g., a computer, server, etc) that carries out the instructions of a computer program as the primary element for carrying out the data-processing functions of such a computer (not shown). Processor 202 may also be implemented as a microprocessor, which incorporates most or all of the functions of a CPU on a single IC (Integrated Circuit) or a group of electronically interlinked IC's.

The memory 204 may be, for example, a flash memory or another non-volatile computer storage medium that can be electrically erased and reprogrammed. Memory 204 may be, for example, a memory card or even a USB flash drive for general storage and transfer of data between computers and other digital products. In some embodiments, memory 204 can also be a specific type of EEPROM (Electrically Erasable Programmable Read-Only Memory) that is erased and programmed in large blocks; in early flash the entire chip had to be erased at once.

The system 200 can be configured to further include a controller 206, which may be, for example, a chip or extension card that interfaces with the devices 102 and 104, and can function as a link to the memory 204 and devices external to system 200.

Figure 3:
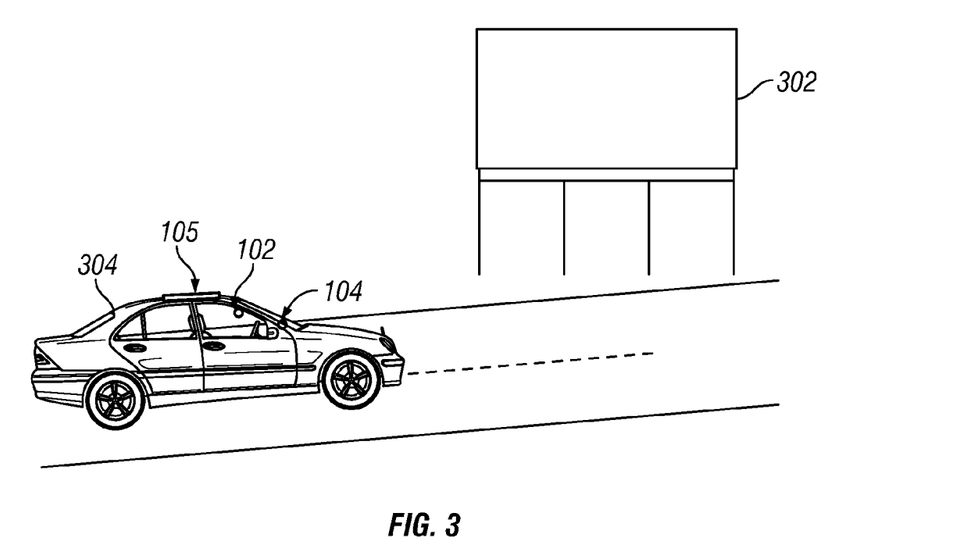
FIG. 3 illustrates a pictorial diagram of a vehicle equipped with an eye tracking device and a surveillance device, in accordance with the disclosed embodiments.

FIG. 3 illustrates a pictorial diagram of the vehicle 304 equipped with the eye tracking device 102 and the surveillance device 104, in accordance with the disclosed embodiments. The eye tracking device 102 can be mounted within the vehicle 304 in a strategic location, such as, for example on or near a rear view mirror located proximate to the front passenger seat. Alternatively, the eye tracking device 102 can be located at other positions in the vehicle 304 or can be composed of a number of eye tracking devices within the vehicle 304. The surveillance device 104 can be located and attached to the vehicle 304 at, for example, one of the side mirrors of the vehicle 304. It can be appreciated that the surveillance device 104 can be located at other positions on the vehicle or can be composed of a group of such surveillance devices at strategic locations on the vehicle 304.

Thus, one or more eye tracking devices such as the eye tracking device 102 can be attached to a mirror (e.g., the rear view mirror) of vehicle 304 or another area of the vehicle 304 that are in view of the driver and that enables the driver's eye(s) to be tracked as it moves to look at surrounding display information and media, such as billboard 302 or other media such as digital signage, window displays, etc. The second device (not shown in FIG. 3), is also attached to the vehicle 304 to provide a view of the surrounding information outside the vehicle 304, such information displayed on the billboard 302.

The views are correlated based on the eye tracking input for the direction of the visual view of the outside area and the second device 104 view of the outside area. Thus, the paired devices 102 and 104 can enable tracking the eye(s) of the driver of the vehicle 304 and tracking the outside display devices in the field of view, and the information would be correlated to provide positive information about the signage information viewed by the driver of the vehicle 304. In advertising terms this can be related to proof of performance or "posting" for the display information. Note that in some embodiments, an optional solar powered device can be utilized to supply electrical energy to the various components, such as devices 102, 104, and so forth. Such a solar powered device can include a solar panel located on the vehicle 304.

Figure 4:
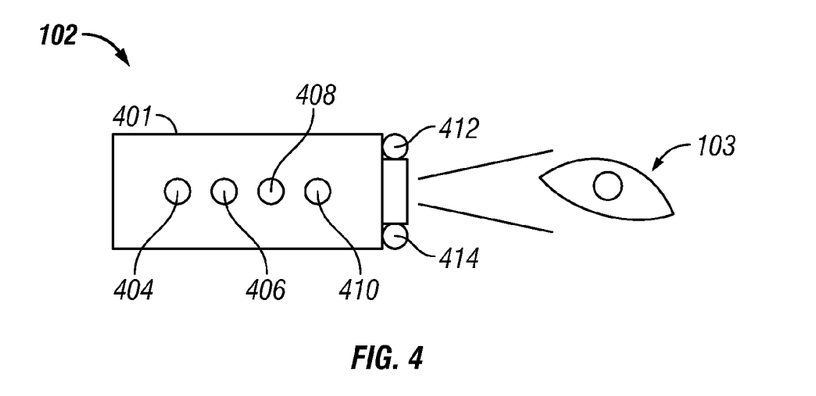
FIG. 4 illustrates a schematic diagram of a particular eye tracking device, in accordance with an embodiment.

FIG. 4 illustrates a schematic diagram of a particular eye tracking device, in accordance with an embodiment. Note that the eye tracking device 102 can be implemented in the context of different embodiments. For example, in one embodiment, the eye tracking device 102 can be configured as a palm-sized video camera 401 surrounded by one or more light emitting diodes, such as, for example, infrared light emitting diodes 404, 406, 408, 410, 412 and 414. Such a device 102 can be configured to record eye contact with, for example, 15-degree accuracy at a distance of around 33 feet, depending upon design consideration. A simple glance from a passenger in the vehicle 304, for example, can record an impression which is utilized to compute a tally that enables measurement metrics that advertisers (e.g., associated with billboard 302) may rely upon for accurate advertising data.

It can be appreciated, of course, that the eye tracking device 102 can be implemented utilizing a number of eye tracking devices and techniques. The eye tracking device 102 can be configured to measure either the point of gaze (i.e., where the individual is looking) or the motion of an individual's eye (or eyes) relative to his or her head. The eye tracking device 102 can measure eye positions and/or eye movement. The eye tracking device 102 can utilize a non-contact and optical component and methodology for measuring eye movement. Light, typically infrared, is reflected from the eye and can be sensed by a video camera, such as, for example, the video camera 401 or some another designed optical sensor.

In some embodiments, information can be then analyzed to extract eye rotation from changes in reflections. A video based eye tracker, for example, typically utilizes the corneal reflection and the center of the pupil as features to track over time. A more sensitive type of eye tracker, such as the dual-Purkinje eye tracker, can utilize reflections from the front of the cornea and the back of the lens as features to track. A still more sensitive method of tracking involves the imaging of features from inside the eye, such as the retinal blood vessels, and follows these features as the eye rotates. Optical methods, particularly those based on video recording, are preferably utilized for gaze tracking and are favored for being non-invasive and inexpensive.

Another example of an eye tracking device and related components and methodologies that can be utilized to implement the eye tracking device 102 is disclosed in U.S. Patent Application Publication No. US20030142041A1 entitled "Eye Tracking/HUD System" which was published on Jul. 31, 2003 by Barlow et al. U.S. Patent Application Publication No. US20030142041A1, which is incorporated herein by reference, describes an apparatus for eye tracking, including: an illuminator; reflection apparatus to reflect illumination from the illuminator onto a surface of a windshield of a vehicle in which the windshield is installed, such that the illumination is reflected onto at least an eye of a person in the vehicle, and to reflect an image of the at least an eye, and a sensor to receive a reflection of the image of the at least an eye reflected by the reflection apparatus and to produce an output signal representative thereof. It can be appreciated, of course, that the device of U.S. Patent Application Publication No. US20030142041A1 is discussed herein for general exemplary and illustrative purposes only and is not considered a limiting feature of the disclosed embodiments.

The surveillance device 104 can be implemented as, for example, a digital video camera for obtaining a view of the areas and in particular media, such as billboards, located in view of the individual in the vehicle 304 as the vehicle 304 passes by such a billboard or other outdoor advertising medium.

Figure 5:
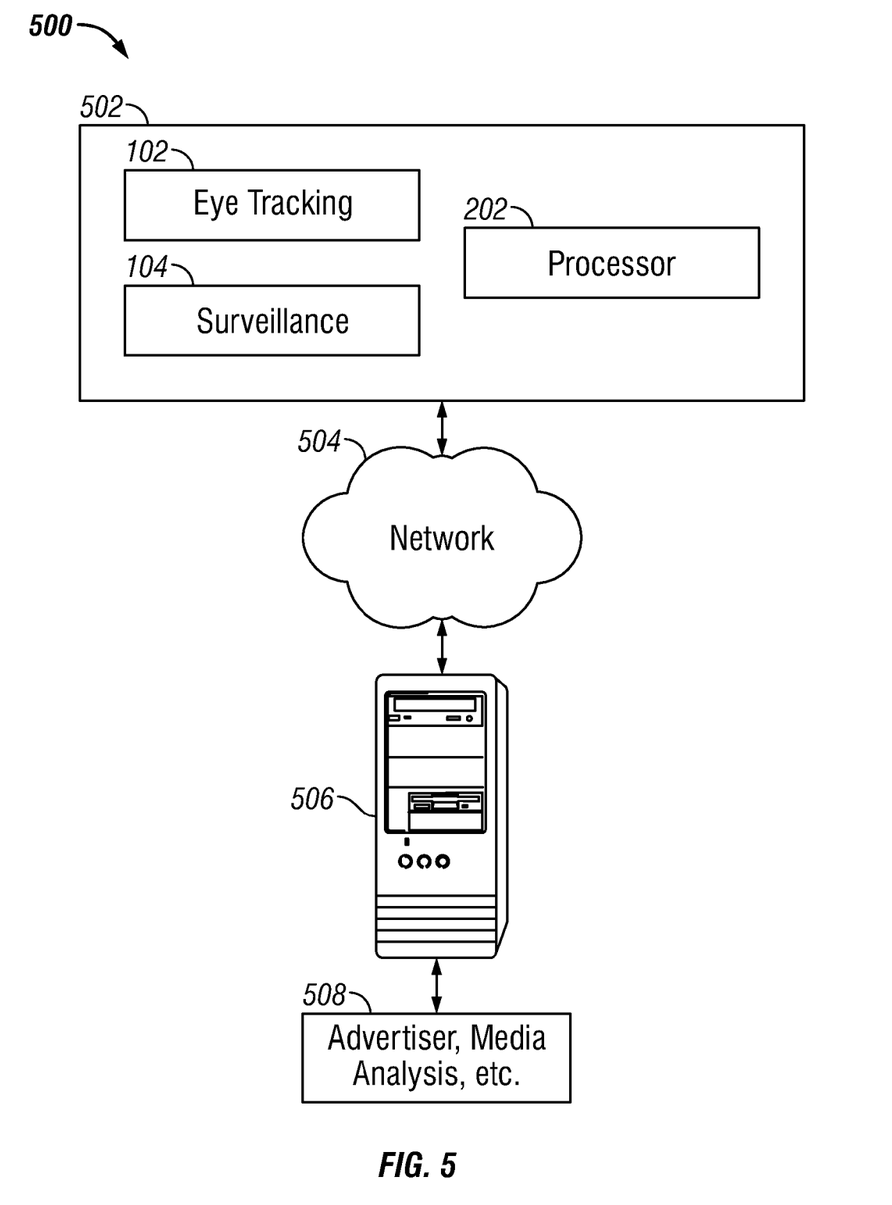
FIG. 5 illustrates a block diagram of a system for monitoring media viewing activity, in accordance with the disclosed embodiments.

FIG. 5 illustrates a block diagram of a system 500 for monitoring media viewing activity, in accordance with the disclosed embodiments. In the particular embodiment depicted in FIG. 5, a system 502 is illustrated, which is composed of the eye-tracking device 102, the surveillance device 104, and the processor 202. The system 502 can communicate with a network 504, which in turn communicates with one or more servers, such as a server 506. The network 504 may comprise, for example, a cellular communications network, which is a radio network composed of radio cells (or simply "cells") served by at least one fixed-location transceiver known as a cell site or base station. These cells cover different and areas to provide radio coverage over a wider area than the area of one cell, so that a variable number of portable transceivers can be used in any one cell and moved through more than one cell during transmission.

Network 504 may also constitute, for example, a wireless network such as an 802.11 network and variations thereof. In other embodiments, network 504 can be, for example, the Internet, which is the global system of interconnected computer networks that use the standardized Internet Protocol Suite (TCP/IP) to serve billions of users worldwide. The Internet is a network of networks that includes millions of private and public, academic, business, and government networks of local to global scope that are linked by copper wires, fiber-optic cables, wireless connections, and other technologies. The Internet carries a vast array of information resources and services, most notably the inter-linked hypertext documents of the World Wide Web (WWW) and the infrastructure to support electronic mail.

As indicated by the embodiment depicted in FIG. 5, data can be collected by the eye tracking device 102 and the surveillance device 104 and processed by the processor 202 and then automatically uploaded via a wireless interface through network 504 (e.g., cellular network, WiFi, etc) to one or more server(s) 506, where such data can be stored and then retrieved by an advertiser 504 or other media analyst for evaluation and review.

Figure 6:
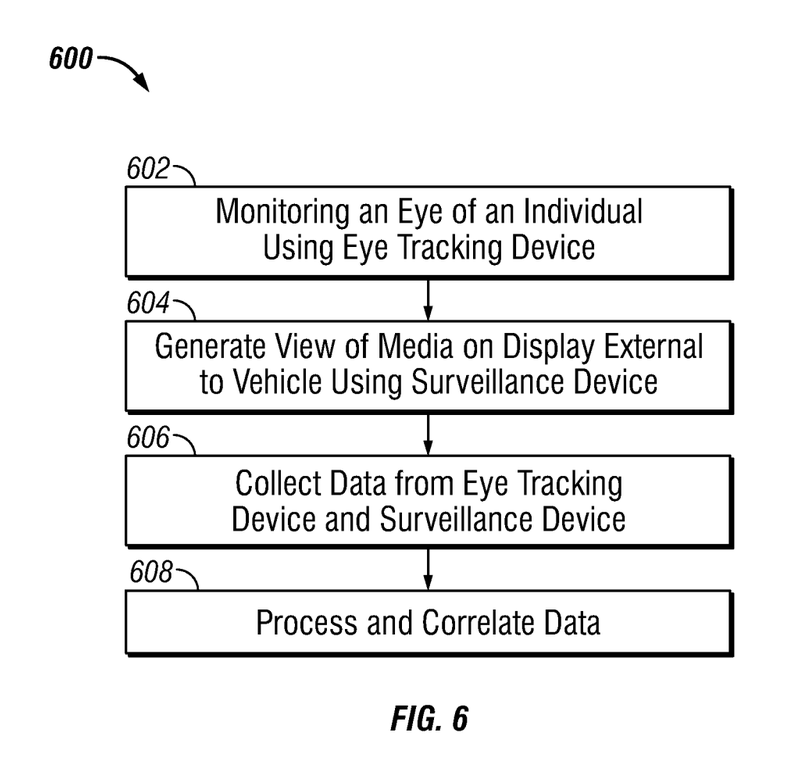
FIG. 6 illustrates a high-level flow chart depicting logical operation steps of a method for tracking mobile viewers of media advertising, in accordance with the disclosed embodiments.

FIG. 6 illustrates a high-level flow chart depicting logical operation steps of a method 600 for tracking mobile viewers of media advertising, in accordance with the disclosed embodiments. It can be appreciated that the various steps depicted in FIG. 1 can be implemented in some embodiments by executing a program instruction in a data-processing apparatus, such as a processor, a computer, a server, etc.

As indicated at block 602, an operation can be implemented for monitoring the eye(s) of an individual in a vehicle utilizing an eye tracking device, such as, for example, eye tracking device 102, and with respect to information displayed on media (e.g., billboards) external to the vehicle and in view of the individual. Next, as depicted at block 604, a view of the information displayed on media external to the vehicle can be generated utilizing a surveillance device that communicates with the eye tracking device.

Thereafter, as described at block 606, data can be collected from the eye tracking device and the surveillance device. Next, as indicated at block 608, the data collected from the surveillance device and the eye tracking device can be processed and correlated such that the data is indicative of a positive posting of the information and can be utilized to enable a valuation of the displayed information (e.g., advertisements). The method 600 thus enables eye tracking for mobile viewers in vehicles (automobiles or similar), including correlation of the eye movement and outdoor view to the actual surrounding billboard display devices.

Figure 7:
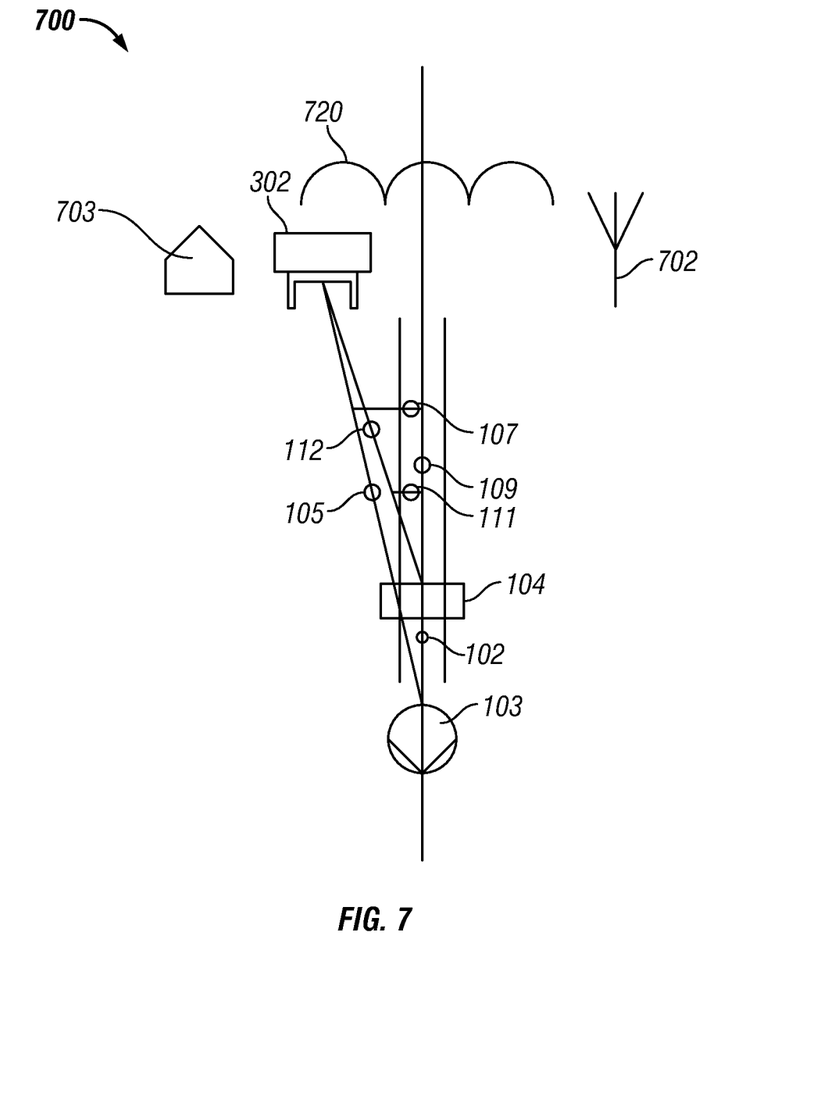
FIG. 7 illustrates a schematic diagram of a system for monitoring media viewing activity, in accordance with the disclosed embodiments.

FIG. 7 illustrates a schematic diagram of a system 700 for monitoring media viewing activity, in accordance with the disclosed embodiments. System 700 includes one or more eye tracking devices, such as, for example, eye tracking devices 102 located on-axis of a roadway or a vehicle field of view. System 700 further includes the surveillance device 104, which monitors external objects such as a building 703, the billboard 302 and so forth, while the eye tracking devices such as 102 monitor the human eye 103 of a passenger or a driver in the vehicle 304. An antenna 702 may be utilized to wirelessly transmit information to and from the network 504 as discussed earlier.

Thus, in the configuration depicted in FIG. 7, a scene is depicted which includes the billboard 302 with content and located near a building or house 703 with, for example, mountains 720 in the background and the antenna 702. Angles, from the eye-to-billboard such as angle 107 and device-to-billboard such as angle 111, are depicted in FIG. 7, which indicate the analytical process for measuring and correlating the view as seen by each detector. Detection of the angle 111 from on-axis centerline of the roadway 109 for the surveillance monitor 104 to the billboard 302, represented by line 112, can be correlated to the angle 107 from on-axis of the roadway 109 for the eye 103 to the billboard 302, represented by line 105, thereby confirming the eye is looking at the billboard 302 in the field of view of the surveillance monitor 104.

Figure 8:
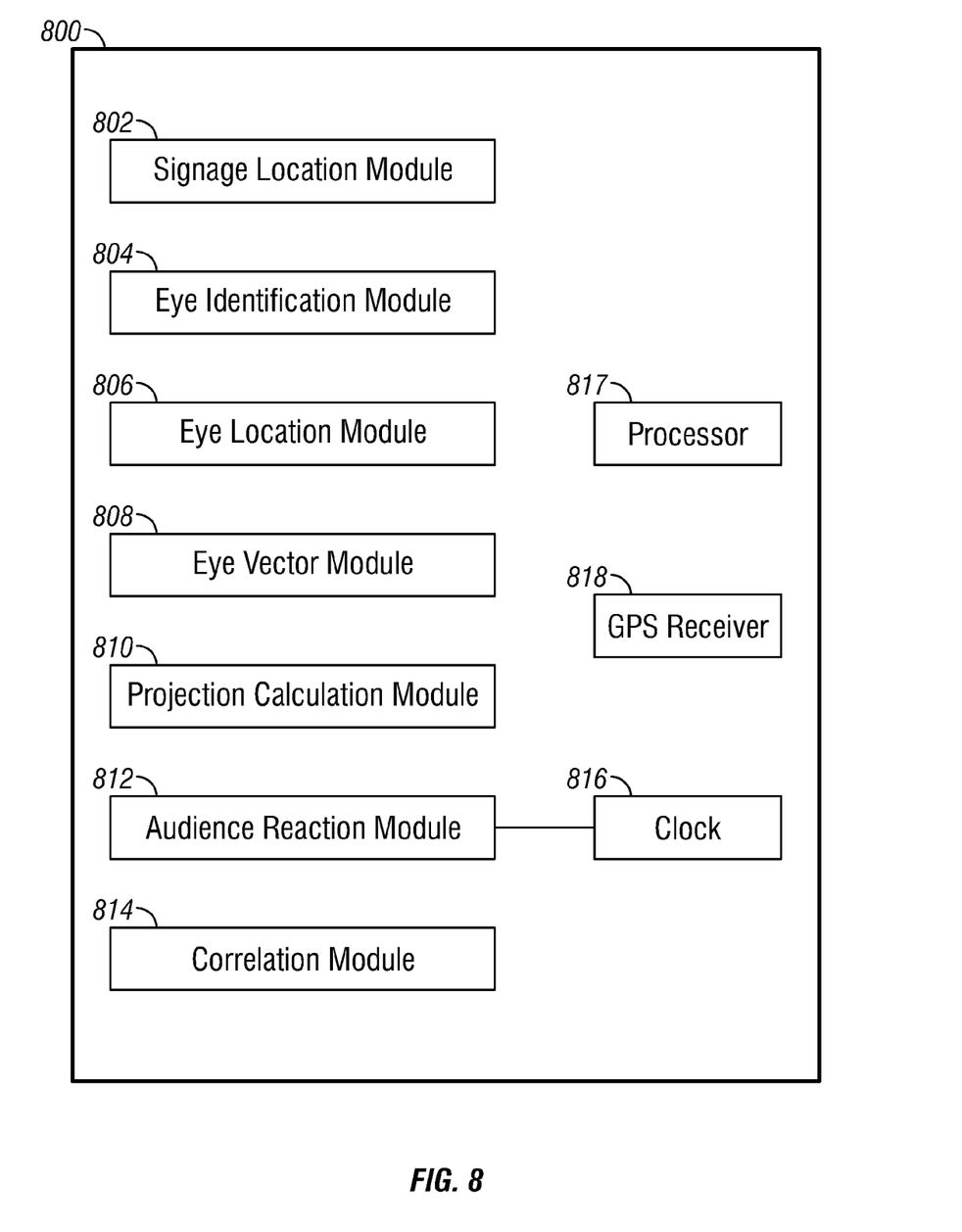
FIG. 8 illustrates a block diagram of an audience reaction system, in accordance with the disclosed embodiments.

FIG. 8 illustrates an audience reaction system 800 in accordance with another embodiment. The system 800 can include a signage location module 802, an eye identification module 804, an eye location module 806, an eye vector module 808, a projection calculation module 810 and an audience reaction module 812. It can be appreciated that such modules can be implemented as physical hardware components and/or software modules, including computer-implementable instructions for performing particular tasks, such as signage location, eye identification, eye location, eye vector calculations, projection calculations, audience reaction processing and so forth.

In some embodiments the signage location module 802 can receive input regarding sign locations wherein sign owners and advertisers are interested in determining how many impressions are received and any other data associated with the impressions. The sign location module 802 can include a database or other memory location that stores three dimensional locations of the facial surface of the sign. This data can be automatically acquired utilizing, for example, satellite photographs and references to known locations. Thus, sign location module 802 can store a locus of points based on latitude, longitude, elevation coordinates and the dimension of the face of the sign (e.g., billboard 302).

The eye identification module 804 can be, for example, a camera supported by recognition software and the eye identification module 804 can use technologies such as edge detection technology and can provide an output signal to the eye location module 806 after the eye identification module 804 locates one or more human eyes.

In response to the signal from the eye identification module 804, the eye location module 806 can determine a location of the eye. The eye location module 806 can determine a latitude longitude, elevation and speed component of the eye using a global positioning system (GPS) receiver. All locations disclosed herein can be defined using latitude, longitude, and elevation coordinates via a GPS receiver. In some embodiments the eye vector module 808 can monitor the identified eye and can determine a relative direction which the eye is directed from the location of the eye.

The eye vector module as well as the other modules disclosed herein can be on a person, in a vehicle or can be mounted in a fixed location relative to the sign. Using the relative direction and the location of the eye, a projection calculation module 806 can calculate the direction of an individual's visual attention by projecting the relative direction from the eye location and use the locus of points in the sign location module database 802 to determine if the individual is visually engaged with the sign. Thus, if the projection of the eye direction from the location of the eye intersects the second location (locus of points) within a particular range such as for example 5,000 feet from the eye to the sign location eye projection module 806 can send a signal to the audience reaction module 812.

In response to the signal the audience reaction module can monitor additional parameters such as duration of eye contact with the sign, scanning of the sign, changes in features of the face such as smiling etc. These changes can be converted into advertising metrics such as number of impressions, duration of attention, demographic information of the viewer, what kind of car the viewer is in, what the viewer is wearing, how fast moving etc.

The system can include a correlation module 814 to correlate what is being displayed on the sign when the individual is engaged with the sign. The correlation module 814 can utilize a clock and the audience reaction module can use a clock to correlate data by time stamping the data. The audience reaction module can use the clock to determine a duration that the eye is directed in particular direction and average engagement times can be calculated for many viewers different audiences etc.

The audience reaction module 812 logs in "real time," a number of different eyes that are directed towards the sign. The audience reaction module 812 can also log changes in facial features or other actions or gestures before during and after an individual views a sign. For example, the audience reaction module 812 can determine if the individual takes an action like closing their eyes, quickly focusing back on the road, reaches for or activates a cell phone or the dials on a radio. The eye vector module can calculate a field of view range in degrees based on the proximity of the eye to the sign and the width of the sign and can also determine a particular location on the sign (e.g., billboard 302) the individual is focusing on.

In some embodiments, the eye vector module 808 can use a velocity of the eye as determined by the eye location module to determine if the projection intersects the billboard location and to improve the accuracy of the system. In some embodiments the audience reaction module can determine the affects of viewer speed using advertising metrics and the reactions made by the individual when viewing the signage. All of the modules 802-814, for example, can employ a processor (or a group of processors) to process and correlate data (e.g., data collected by the audience reaction module). Monitoring can be performed on digital billboards where the face provides a dynamic or digital display.

System 800 thus can include the use of the signage location module 802 to provide a first location of a sign. The eye identification module 804 can transmit a signal in response to locating an eye of a human. The eye location module 806 can determine a second location of the eye in response to the signal. The eye vector module 808 can determine a first relative direction to which the eye is directed from the second location. The projection calculation module 810 can be utilized to project the first relative direction from the second location of the eye and determine if the projection intersects the first location of the sign. The audience reaction module 812 can monitor at least the eye and determine an advertising metric.

Additionally, the eye vector module 806 can determine the relative direction in one dimension. In other embodiments, system 800 can be configured to further include a correlation module 814 to correlate what is displayed on the sign with the advertising metric. A clock 816, can also be coupled to the audience reaction module 812 to time stamp the advertising metric. The audience reaction module 812 can utilize the clock determine a minimum time that the eye is directed in particular direction. The first and second location can be defined, for example, in latitude and longitude coordinates. In some embodiments, the audience reaction module 812 can log in real time, a number of different eyes that are directed towards the sign.

Additionally, the audience reaction module 812 can log changes in facial features. The eye vector module 808 can also, in some embodiments, be located in a vehicle, such as, for example, vehicle 304 illustrated and described herein. The eye vector module 808 can be mounted in a fixed location relative to the sign. The eye vector module 808 can calculate a field of view range based on the first location the second location and a dimension of the face of the sign. Additionally, in some embodiments, the projection calculation module 810 can detect the velocity associated with the eye and utilize the velocity to determine if the projection intersects the second location. A processor 817 can also communicate with each of the aforementioned modules and can process and correlate data collected by the audience reaction module 812. The sign (e.g., billboard 302) can, in some embodiments, constitute a dynamic digital display.

System 800 can also, in some embodiments, utilize a GPS (Global Positioning Satellite) receiver 818 to determine one of the first location or the second location. The GPS receiver 818 can be configured to communicate with each of the aforementioned modules along with the processor 817, etc. Note that in other embodiments, the signage location module 802 can accept three dimensional sign location data from the GPS receiver 818 and store the sign location data in a database or other appropriate memory location (not shown in FIG. 8). The eye location module 806 can also utilize the GPS receiver 818 to determine the second location. The first location can additionally be acquired using satellite transmissions.

It will be appreciated that variations of the above-disclosed and other features and functions, or alternatives thereof, can be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. An audience reaction system comprising:
   an eye vector module, the eye vector module attached at one or more of: a location within a vehicle or a location external to the vehicle, and facing at least one individual travelling in the vehicle, the eye vector module measuring an eye of the at least one individual relative to an axis of a roadway;
   a surveillance device attached to the vehicle at a first location and facing externally to the vehicle, the surveillance device monitoring a sign located external to the vehicle and off the axis of the roadway;
   a processor enabled to perform the following steps:
      determine a second location representing a location of the sign and generate a view of the sign, at least one advertisement displayed on the sign;
      receive a signal in response to the eye vector module determining a third location, velocity, and orientation of the eye of the at least one individual travelling in the vehicle on the roadway;
      calculate a projection in a first relative direction, based on the first, second and third locations, and velocity and orientation of the eye, wherein calculating the projection includes:
         determining a surveillance device-to-sign angle measured from the axis of the roadway at the first location to the second location;
         determining an eye-to-sign angle measured from the axis of the roadway at the third location to the second location;
      determine whether the projection intersects the second location of the sign, utilizing a projection calculation module, wherein the determination is made at least in part based on a correlation of the surveillance device-to-sign angle and the eye-to-sign angle; and
      in response to determining that the projection intersects the second location of the sign:
         identify an advertisement displayed on the sign, based on the view of the sign,
         correlate the view of the sign with the particular advertisement displayed on the sign to determine an advertising metric for the particular advertisement, utilizing an audience reaction module.

2. The system of claim 1, wherein the eye vector module determines a relative direction in one dimension.

3. The system of claim 1, wherein:
   the processor is further configured to correlate what is displayed on the sign with the advertising metric utilizing a correlation module, and
   the advertising metric identifies a type of vehicle being driven by the at least one individual.

4. The system of claim 1 further comprising a clock coupled to the audience reaction module capable of time stamping the advertising metric.

5. The system of claim 4, wherein the audience reaction module is capable of using the clock to determine a minimum time period that the eye is directed in a particular direction.

6. The system of claim 1, wherein the second location and the third location are defined in latitude longitude coordinates.

7. The system of claim 1, wherein the audience reaction module is capable of logging in real time a number of different eyes that are directed towards the sign.

8. The system of claim 1, wherein the audience reaction module is capable of logging changes in facial features.

9. The system of claim 1, wherein the location within a vehicle includes a rear-view mirror of the vehicle.

10. The system of claim 1, wherein the location external to the vehicle includes a fixed location relative to the sign.

11. The system of claim 1, wherein eye vector module is capable of calculating a field of view range based on the second location, the third location, and a dimension of a face of the sign.

12. The system of claim 1, wherein the projection calculation module is capable of detecting a velocity associated with the eye and is capable of utilizing the velocity to determine if the projection intersects the second location.

13. The system of claim 1, wherein the sign has a dynamic digital display.

14. The system of claim 1, wherein the processor is further configured to determine one of the second location or the third location utilizing a signage location module and a global positioning receiver.

15. The system of claim 14, wherein the signage location module is capable of accepting three dimensional sign location data from the global positioning system and is capable of storing the three dimensional sign location data in a database.

16. The system of claim 14, wherein the eye location module is capable of using a global positioning receiver to determine the third location.

17. The system of claim 1, wherein the processor is further configured to acquire the second location using satellite transmissions and a satellite communications receiver.

18. A system for monitoring media viewing activity, said system comprising:
an eye tracking device attached to a vehicle, the eye tracking device configured to generate eye tracking data including a location, velocity, and orientation associated with at least one eye of at least one individual riding in a vehicle travelling on a roadway, the at least one eye moving with respect to information displayed on media external to said vehicle, the media in view of said at least one individual;
a surveillance device attached to said vehicle, the surveillance device configured to generate an external view of said information displayed on media external to said vehicle;
a processor configured to process and correlate said eye tracking data and said external view to:
identify said information displayed on media external to said vehicle as a particular advertisement, and
create an advertising metric by determining that the at least one individual is viewing said particular advertisement;
wherein correlating the eye tracking data and the external view includes:
determining a surveillance device-to-media angle measured from a location of the surveillance device within an axis of the roadway relative to a location of the media;
determining an eye-to-media angle measured from the location of the eye within an axis of the roadway and an orientation relative to the media; and
correlating the surveillance device-to-media angle and the eye-to-media angle to determine an intersection.

19. The system of claim 18, wherein said media comprises at least one static billboard.

20. The system of claim 18, wherein said media comprises at least one digital sign.

21. The system of claim 18, wherein said media comprises at least one window display.

22. The system of claim 18 further comprising a solar powered device for providing electrical energy to said eye tracking device and said surveillance device.

23. The system of claim 18, wherein the eye vector device is coupled to a mirror of the vehicle.

24. A method for monitoring media viewing activity, said method comprising:
monitoring, by utilizing an eye tracking device attached to a mirror of a vehicle and configured to generate eye tracking data including a location, velocity, and orientation of at least one eye of at least one individual in the vehicle with respect to information displayed on media external to said vehicle and in view of said at least one individual, by executing a program instruction in a data-processing apparatus; and
generating a view of said information displayed on media external to said vehicle by utilizing a surveillance device attached to the vehicle, wherein the surveillance device communicates with said eye tracking device;
correlating, utilizing a processor, data collected from said surveillance device and said eye tracking device, said data indicative of:
identification of said information as a particular advertisement, based on the view of said information generated by said surveillance device,
a positive posting of said particular advertisement to thereby enable a valuation of said particular advertisement displayed on said media;
wherein correlating data collected from the surveillance device and the eye tracking device includes:
determining a surveillance device-to-media angle measured from a location of the surveillance device within an axis of a roadway to a location of the billboard;
determining an eye-to-media angle measured from the location of the eye within an axis of the roadway to the location of the media; and
correlating the device-to-media angle and the eye-to-media angle to determine an intersection.

25. The method of claim 24, wherein correlating said data collected from said surveillance device and said eye tracking device is performed by executing a program instruction in a data-processing apparatus.

26. The method of claim 24, wherein said first vehicle surface is an interior vehicle surface and said second vehicle surface is an exterior vehicle surface.

27. The method of claim 24, wherein said media comprises at least one of the following:
a static billboard;
a digital sign; and
a window display.

28. The method of claim 24 further comprising providing electrical energy to said eye tracking device and said surveillance device via a solar powered device.

29. The method of claim 24 further comprising storing in a memory information output by said eye tracking device and said surveillance device by executing a program instruction in a data-processing apparatus.

30. The method of claim 24, wherein the eye tracking device includes one or more infrared light emitting diodes.

31. A non-transitory computer readable medium having stored thereon a set of instructions that are executable by at least one processor of a computer system to carry out a method comprising:
receiving eye tracking data from an eye tracking system facing an occupant of a vehicle, the eye tracking system including an eye tracking device attached to a mirror of the vehicle;
receiving external video data from a surveillance system facing information displayed on media external to the vehicle, the surveillance system including a surveillance device attached to the vehicle;

processing the eye tracking data and the external video data to:
- identify the information displayed on the media as a particular advertisement, based on the external video data, and
- determine that the at least one eye of the occupant has viewed the particular advertisement, based on a projected intersection of the occupant's line of sight and the particular advertisement, wherein the determination includes:
  - determining a surveillance device-to-media angle measured from a location of the surveillance device within an axis of the roadway to a location of the billboard;
  - determining an eye-to-media angle measured from a location of the eye within an axis of the roadway to a location of the media;
  - correlating the surveillance device-to-media angle and the eye-to-media angle to determine if the projected intersection occurred; and transmitting the processed eye tracking data and processed external video data via a network.

32. The non-transitory computer readable medium of claim 31, wherein the eye tracking system further includes a plurality of eye tracking devices.

33. The non-transitory computer readable medium of claim 31, wherein the processed eye tracking data and processed external video data is transmitted to one or more servers.

34. The non-transitory computer readable medium of claim 33, wherein the processed eye tracking data and processed external video data is stored on at least one server.

35. The non-transitory computer readable medium of claim 31, wherein the network includes a cellular network.

36. The non-transitory computer readable medium of claim 31, wherein the network includes the Internet.

37. The non-transitory computer readable medium of claim 31, wherein processing the eye tracking data and the external video data includes correlating the eye tracking data to the external video data.

* * * * *